United States Patent [19]

Gustin

[11] 4,102,814

[45] Jul. 25, 1978

[54] OXYGEN SCAVENGER IN ELEMENTAL COMBUSTION ANALYSES

[75] Inventor: Grant M. Gustin, Oxford, N.Y.

[73] Assignee: Morton-Norwich Products, Inc., Norwich, N.Y.

[21] Appl. No.: 722,563

[22] Filed: Sep. 13, 1976

[51] Int. Cl.$^2$ ............................................. C09K 3/00
[52] U.S. Cl. ............................... 252/408; 23/230 PC; 106/290; 106/288 B; 252/454; 252/182
[58] Field of Search .................. 23/230 PC; 252/408; 106/290, 288 B, 454

[56] References Cited

U.S. PATENT DOCUMENTS

| | | | |
|---|---|---|---|
| 3,464,795 | 9/1969 | Schmitt et al. | 23/230 PC |
| 3,853,474 | 12/1974 | Austin | 23/230 PC |
| 3,945,799 | 3/1976 | Honma | 23/230 PC |
| 3,985,505 | 10/1976 | Bredeweg | 23/230 PC |
| 4,025,309 | 5/1977 | Hack | 23/230 PC |

*Primary Examiner*—Benjamin R. Padgett
*Assistant Examiner*—J. L. Barr
*Attorney, Agent, or Firm*—Anthony J. Franze

[57] ABSTRACT

A porous copper reagent, useful in elemental combustion analyses, prepared from a mixture of cupric oxide and inert diatomaceous earth is described.

1 Claim, No Drawings

OXYGEN SCAVENGER IN ELEMENTAL COMBUSTION ANALYSES

This invention is concerned with the provision of a copper reagent useful in elemental analyses. In greater particularity this invention has as its object the provision of porous copper granules blended with a porous, inert, dimensionally stable powder having utility in combustion analyses.

Copper has been used as an oxygen scavenger in combustion chemistry for at least 75 years. In the presently employed multi-element analyzers for carbon, hydrogen and nitrogen, it reduces nitrogen oxides to nitrogen and removes the oxygen gas used in the combustion process quantitatively at temperatures above 600° C. To enhance its capacity for oxygen, copper in the form of coiled wire was first replaced by copper turnings and later with copper granules. Notwithstanding these advancements total utilization of copper was not achieved for such forms permitted oxygen to escape after only 5-10% of its theoretical oxygen scavenging capacity had been consumed. Such inefficient oxygen capturing requires frequent and costly replacement or regeneration of the copper.

I have now discovered that the capacity of copper in combustion analyses procedures can be increased to about 97% of its theoretical capacity by blending it with an inert, porous, diatomaceous earth such as Chromosorb P, Johns-Manville Celite Division, New York, New York.

In accordance with my discovery a thick slurry of cupric oxide, prepared by boiling and thoroughly washing the precipitate formed by bringing together a solution of a copper salt such as cupric sulfate and a solution of sodium hydroxide, was blended with finer than 100 USP mesh Chromosorb P at a weight ratio of 6 parts copper to 1 part Chromosorb P. The thoroughly washed slurry was filtered, partially dried on the filter, and then pressed through a 20 USP mesh screen with a spatula. The extruded material was dried at 100°-120° C. The resulting friable spaghetti-like granules were reduced at 400°-500° C with hydrogen in a nitrogen carrier gas. The exothermic heat of reaction created a visible red glowing zone which was maintained at a dull to medium red (700°-1000° C) by adjusting the hydrogen gas flow. Heating during this first reduction step shrank the granules 5 fold. Subsequent oxidation with air at 500°-700° C caused additional shrinkage and strengthening of the granules. A constant volume was attained on the fourth reduction oxidation cycle. The copper granules remained porous in appearance and the oxygen capacity was about 97% of theory. This capacity was not diminished after two years of constant use.

A surprising feature of my invention is the absence of expansion and sintering of the oxidized granules into a solid mass. Air drawn through it when heated caused a brilliant red glow ($>1000°$ C), yet the oxidized granules flowed easily from the tube. Also an important feature is the lack of tarnished copper normally appearing beyond the main oxidation zone.

The ultimate test of my invention is its use in an analyzer's reduction tube (330 mm × 11 mm OD). The 280 mm packing of copper/Chromosorb, preshrunk to constant volume, weighed 20 g, 1/5th the normal weight of copper reagent ordinarily used yet the packing life span was increased 2.5 times. After 164 analyses (6 days of use at 650°-700° C) the reduction tube was removed for inspection. A 30 mm length of unused copper packing remained, equivalent to 20 further analyses based on 164 analyses/250 mm oxidized packing. The oxygen weight gain in the initial 250 mm portion was 3.59 g; 97% of its theoretical capacity. Excellent carbon, hydrogen, and nitrogen results were consistently obtained. No deviation from results previously obtained using conventional copper granules were evident.

What is claimed is:

1. A copper reagent useful in combustion analyses consisting of a granular mixture of copper and a porous, inert, diatomaceous earth of a fineness greater than 100 USP mesh in which the ratio of copper to said earth is 6:1 w/w.

* * * * *